(12) United States Patent
Oguchi

(10) Patent No.: US 9,206,459 B2
(45) Date of Patent: Dec. 8, 2015

(54) DETECTION AND DECOMPOSITION OF BISPHENOL-A

(75) Inventor: Shinobu Oguchi, Tokyo (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 228 days.

(21) Appl. No.: 12/999,469

(22) PCT Filed: Jun. 11, 2010

(86) PCT No.: PCT/US2010/038289
§ 371 (c)(1),
(2), (4) Date: Dec. 16, 2010

(87) PCT Pub. No.: WO2011/155943
PCT Pub. Date: Dec. 15, 2011

(65) Prior Publication Data
US 2011/0303554 A1    Dec. 15, 2011

(51) Int. Cl.
*C12Q 1/00* (2006.01)
*G01N 27/327* (2006.01)

(52) U.S. Cl.
CPC ............ *C12Q 1/005* (2013.01); *C12Q 1/001* (2013.01); *G01N 27/3275* (2013.01); *G01N 27/3276* (2013.01); *Y10S 435/817* (2013.01)

(58) Field of Classification Search
CPC .... C12Q 1/001; C12Q 1/005; Y10S 435/817; G01N 27/3275; G01N 27/3276
USPC ............ 204/471, 472, 483, 486, 403.01, 204/403.04, 403.05, 403.06, 403.1, 403.12, 204/403.14; 427/2.1, 2.11; 205/777.5
See application file for complete search history.

(56) References Cited

U.S. PATENT DOCUMENTS

| | | | | |
|---|---|---|---|---|
| 6,267,866 | B1 * | 7/2001 | Glesener et al. | 205/450 |
| 6,814,845 | B2 * | 11/2004 | Wilson et al. | 204/486 |
| 7,638,228 | B2 * | 12/2009 | Minteer et al. | 429/401 |
| 8,057,683 | B2 * | 11/2011 | Gane et al. | 210/691 |

(Continued)

FOREIGN PATENT DOCUMENTS

| | | |
|---|---|---|
| JP | 2004-180656 A1 | 7/2004 |
| JP | 2006-034171 A1 | 2/2006 |

(Continued)

OTHER PUBLICATIONS

Elkaoutit et al, "Dual Laccase-Tyrosinase Based Sonogel-Carbon Biosensor for Monitoring Polyphenols in Beers"; J. Agric. Food Chem. 2007,55,8011-8018.*

(Continued)

*Primary Examiner* — Keith Hendricks
*Assistant Examiner* — Salil Jain
(74) *Attorney, Agent, or Firm* — Workman Nydegger

(57) ABSTRACT

An enzyme electrode that enables rapid degradation of bisphenol-A (BPA) in a contaminated sample and/or monitoring of BPA concentration in a contaminated sample. The enzyme electrode includes a working electrode having one or more selected enzymes that are capable of degrading BPA linked to the working electrode. The selected enzymes linked to the working electrode are capable of degrading BPA at an enhanced rate in response to an applied voltage. The electrode can be used to monitor BPA concentration in a contaminated sample by measuring current flow through the electrode in response to an applied voltage.

9 Claims, 2 Drawing Sheets

(56) References Cited

U.S. PATENT DOCUMENTS

| | | | |
|---|---|---|---|
| 2002/0130069 A1* | 9/2002 | Moskoff | 210/85 |
| 2003/0104119 A1 | 6/2003 | Wilson et al. | |
| 2005/0089977 A1* | 4/2005 | Semba et al. | 435/128 |
| 2008/0178663 A1* | 7/2008 | Yang et al. | 73/61.41 |
| 2010/0315107 A1* | 12/2010 | Matsumoto et al. | 324/693 |

FOREIGN PATENT DOCUMENTS

| | | |
|---|---|---|
| JP | 2008-148662 A1 | 7/2008 |
| WO | 98/35053 A2 | 8/1998 |

OTHER PUBLICATIONS

Tsutsumi et al, "Removal of estrogenic activities of Bisphenol A and nonyl phenol by oxidative enzymes from lignin-degrading basidomycetes"; Chemosphere 42 (2001), 271-276.*

Mita et al, "Enzymatic Determination of BPA by means of Tyrosinase Immobilized on Different Carbon Carriers," Biosensors & Bioelectronics, 23 (2007), pp. 60-65, published in Mar. 2007.*

Kolvenbach, B., et al., "Degradation Pathway of Bisphenol A: Does ipso Substitution Apply to Phenols Containing a Quaternary α-Carbon Structure in the para Position? Applied And Environmental Microbiology," vol. 73, Issue 15, American Society for Microbiology, 4776-4784 (2007).

"Safety information on the endocrine effects of bisphenol A epoxy resin and Acceptable standards of labor safety and (3) bisphenol A," accessed at http://www.epoxy.gr.jp/qa/img/pdf/d6_3.pdf, pp. 2 (Machine Translation) Aug. 1, 2004.

"Development of new detection methods and repair of environmental pollutants by electrochemical method using a functional material," accessed at http://www.ees.hokudai.ac.jp/coe21/J/sympo/PD/terui.pdf, pp. 11 (Machine Translation) Available as of Jul. 27, 2012.

International Search Report dated Sep. 7, 2010, in PCT application No. PCT/US2010/038289 from which the present application has been nationalized in the U.S.

Dominic W.S. Wong, Structure and Action Mechanism of Ligninolyitic Enzymes, Appl Biochem Biotechnol, 2008, pp. 174-209, Humana Press.

Paola Giardina et al., Laccases: a never-ending story, Cellular and Molecular Life Sciences, 2009, pp. 369-385, Birhauser Verlag, Switzerland.

Y. Tsutsumi et al., Removal of Estrogenic Activites of Bisphenonl A and Nonylphenol by Oxidative Enzymes from Lignin-Degrading Basidiomycetes, Chemosphere, 2000, pp. 271-276.

J. Jegan Roy et al, Biosensor for the determination of phenols based on Cross-Linked Enzymes Crystals (CLEC) of laccase, Biosensors & Bioelectronics, 2004, pp. 206-211.

Ulku Anik Kurgoz et al., Laccase Biosensors Based on Mercury Thin Film Electrode, Artificial Cells, Blood Substitutes, and Biotechnology, 2005, pp. 447-456.

Ewa Nazaruk et al., Properties of native and hydrophobic laccases immobilized in the liquid crystalline cubic phase on electrodes, J Biol Inorg Chem, 2007, pp. 335-344.

Jacob N Wohlstadter et al., Carbon Nanotube-BAsed Biosensor, Advanced Materials, 2003, vol. 15, No. 14, pp. 1184-1187.

Chunya Li et al., A novel amperometric sensor and chromatographic detector for determination of parathion, Anal Bioanal Chem, 2005, pp. 1049-1055.

Kangbing Wu et al., Mercury-free simultaneous determination of cadmium and lead at a glassy carbon electrode modified with multiwall carbon nanotubes, Analytica Chemica Acia, 2003, pp. 215-221.

Norifumi Terui et al., Carbon Nanotubes in Environmental Analysis and Remediation, 2004, pp. 158-159.

Yoshiro Sakai, To the Progress in the Research on Chemical Sensors, Chemical Sensors, 1995, vol. 11 No. 1.

Shin-Ichi Ota et al., Electrocatalytic Degradation of Chlorinated Phenolic Compound with Laccase-Modified Polyaniline / Silica Sol-Gel, Carbon Composite Electrodes, Fukuoak Inst. Tech, vol. 40 No. 1, 2007, pp. 21-27.

Pan Xiurong et al., CCQM Working Document on Coulometry, CCQM 99-16, The NRCCRM of China, 1999.

Electrode Geometry 3-0-6 CV, S Corporation agent Bee, Electrochemistry BAS Inc.

Biosphenol A Source of Exposure Study, http://bem.m.chiba-u.ac.jp/SRL/page041.html.

Root T. Yang et al., Measurement of Environmental Hormones, Environmental Analysis II Feature Measurement, Shimadzu Review, 1999, vol. 56, http://shimadzu.co.jp/tec_news/srv56_34/report06.html.

Environmental Hormones in Tap Water, http://subsite.icu.ac.jp/people/yoshino/Y03M10.html.

Toru Ueda et al., Isolation of a BisphenolA-Degrading Beta-Proteobacterium from a Human Stool Sample, Journal of Environmental Biotechnology, 2005, vol. 4, No. 2, pp. 121-126.

Tanaka Shiyunitsu, Development of New Detection and Remediation of Environmental Pollutants by Using Electrochemical Functional Materials.

Reverse Osmosis, http://www.jyousuiki-navi.com/kind/000018.php.

Mohammed Elkaoutit et al., Dual Laccase-Tyrosinase Based Sonogel-Carbon Biosensor for Monitoring Polyphenols in Beers, Journal of Agriculture and Food Chemistry, 2007., pp. 8011-8018.

D.G. Mita et al., Enzymatic Determination of BPA by means of Tyrosinase Immobilized on Different Carbon Carriers, Biosensors and Bioelectronics, 2007, pp. 60-65.

Suna Timur et al., Thick Film Sensors based on laccases from different sources immobilized in polyaniline matrix, Sensors and Actuators, 2004, pp. 132-136.

* cited by examiner

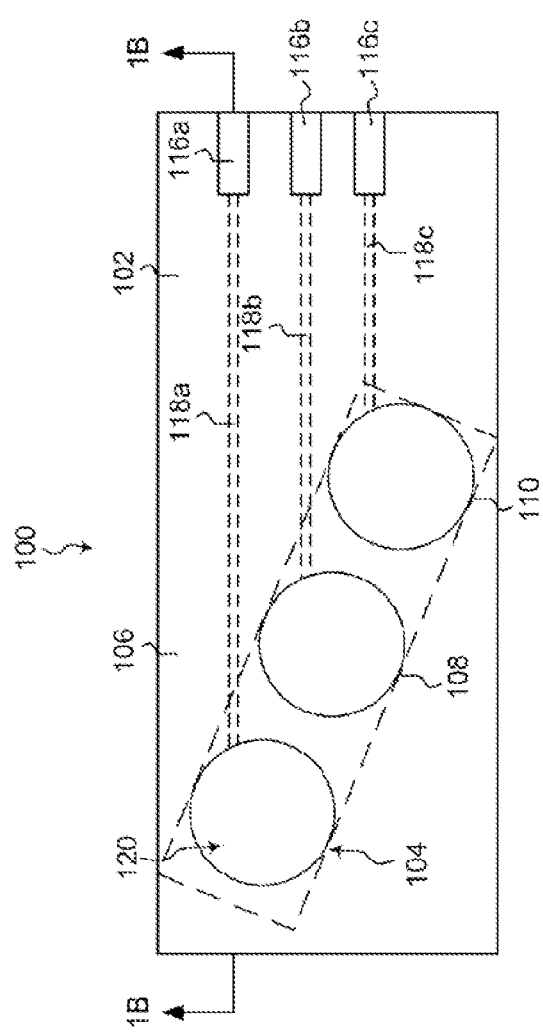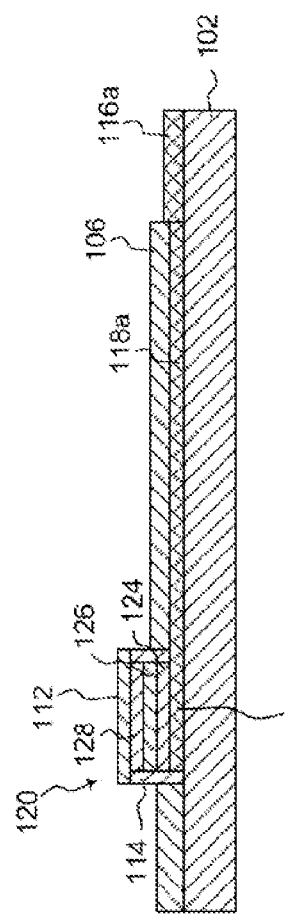
*Figure 1A*
*Figure 1B*

DETECTION AND DECOMPOSITION OF BISPHENOL-A

CROSS-REFERENCE TO RELATED APPLICATIONS

The present application is a U.S. national stage filing under 35 U.S.C. 371 of International Application No. PCT/US2010/038289, filed on Jun. 11, 2010.

BACKGROUND

Bisphenol-A (2,2-bis(4-hydroxyphenyl)propane, BPA) is an organic compound with two phenol functional groups. BPA is a bifunctional building block of several important plastics and plastic additives, including polycarbonate.

BPA is a persistent environmental pollutant that is believed to be an endocrine disruptor that can mimic certain hormones and that may lead to negative health effects. While current safety standards for BPA are in the parts-per-million range, BPA may be able to interfere with endocrine function at concentrations as low as the parts-per-trillion range. Early development appears to be the period of greatest sensitivity to its effects.

The presence or absence of BPA in aqueous media (e.g., water samples from municipal water systems) is typically evaluated by collecting samples that are then transported to a laboratory where they are analyzed by methods such as high performance liquid chromatography (HPLC) and/or immunoassay. There have been cases, however, where BPA was not detected in the treated water in the water supply system, but was detected in the tap water dispensed at the end of the water supply. This is believed to be caused by leaching from the interior coating of the water line pipe.

SUMMARY

Devices and methods are disclosed for removing BPA from contaminated water and/or monitoring bisphenol-A (BPA) concentration in contaminated water. Devices include an enzyme electrode having one or more selected enzymes that are capable of degrading BPA coupled to the electrode. The selected enzymes coupled to the electrode are capable of degrading BPA at an enhanced rate in response to an applied voltage. The electrodes described herein can also be used to monitor BPA concentration in contaminated water by measuring current flow through the electrode in response to an applied voltage.

In one embodiment, an enzyme electrode is configured for detecting and/or degrading bisphenol-A (BPA). The enzyme electrode may include an electrode system that includes a working electrode and an enzyme capable of reacting with BPA linked to the working electrode. Suitable examples of enzymes that can be immobilized to the working electrode include, but are not limited to, ligninases such as laccase, manganese peroxidase (MnP), lignin peroxidase, and the like.

In another embodiment, a method is provided for detecting and/or degrading bisphenol-A (BPA). The method may include providing an electrode system that includes an enzyme capable of reacting with BPA linked to the electrode system, immersing the electrode system in a sample suspected of being contaminated with BPA, and applying a voltage to the electrode system to promote detection and/or degradation of BPA.

In yet another embodiment, a method for degrading bisphenol-A (BPA) is disclosed. The method may include providing an electrode system that includes an electrically insulating base plate, a working electrode, a counter electrode, and an enzyme selected from the group consisting of manganese peroxidase (MnP), laccase, ligninase, and combinations thereof linked to the working electrode, wherein the working electrode includes a carbon electrode, a porous silica gel film linked to the carbon electrode, and an electropolymerized film configured for promoting transfer of electrons to the enzyme immobilized to the working electrode, immersing the electrode system in a sample suspected of being contaminated with BPA, and applying a voltage in a range from about −1 V to about 1 V to the electrode system for a period of time sufficient to degrade the BPA below a selected level.

The foregoing summary is illustrative only and is not intended to be in any way limiting. In addition to the illustrative aspects, embodiments, and features described above, further aspects, embodiments, and features will become apparent by reference to the following detailed description.

BRIEF DESCRIPTION OF THE FIGURES

FIG. 1A depicts a schematic of an illustrative embodiment of an enzyme electrode;

FIG. 1B depicts a cut-away view of the enzyme electrode of FIG. 1A taken along line 1B-1B.

DETAILED DESCRIPTION

I. Introduction

Figure 2:
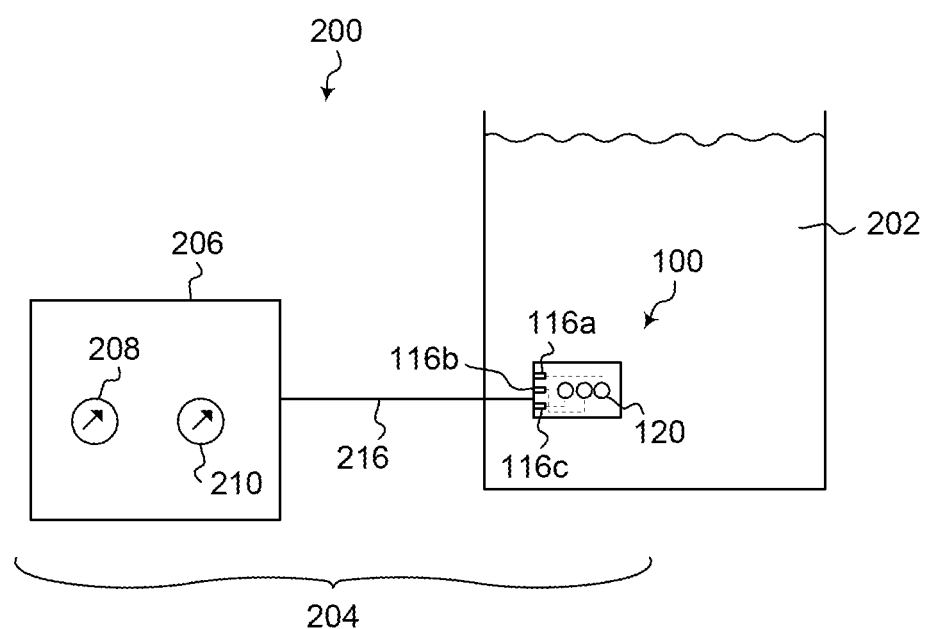
FIG. 2 depicts a schematic of an illustrative embodiment of an enzyme electrode that enables degradation of bisphenol-A (BPA) and/or monitoring of BPA concentration in contaminated water.

In the following detailed description, reference is made to the accompanying Figures, which form a part hereof. In the Figures, similar symbols typically identify similar components, unless context dictates otherwise. The illustrative embodiments described in the detailed description, Figures, and claims are not meant to be limiting. Other embodiments may be utilized, and other changes may be made, without departing from the spirit or scope of the subject matter presented here.

Devices and methods are disclosed for removing BPA from contaminated aqueous solutions including drinking water and water contained in foods. Moreover, devices and methods are disclosed for monitoring bisphenol-A (BPA) concentration in contaminated aqueous solutions including drinking water and water contained in foods. Devices include an enzyme electrode having one or more selected enzymes that are capable of degrading BPA coupled to the electrode. The selected enzymes coupled to the electrode are capable of degrading BPA at an enhanced rate in response to an applied voltage. The electrodes described herein can also be used to monitor BPA concentration in contaminated water by measuring current flow through the electrode in response to an applied voltage.

An enzyme electrode is a chemical transducer that functions by combining an electrochemical probe (e.g., an amperometric, a coulometric, or a conductimetric probe) with an enzyme activity associated with the electrode. In these devices, the enzyme can, for example, be used to selectively degrade a substrate. The enzyme provides selectivity by virtue of its biological affinity for a particular substrate. The electrode can be used to activate the enzyme by setting an electrical potential (i.e., a voltage) that can affect redox state of the enzyme.

Enzymes are proteinaceous molecules that catalyze a myriad of biochemical reactions that occur within living cells. Like their chemical counterparts, enzymes accelerate the rate of chemical reactions without themselves being changed in the overall process. There are many different kinds on enzymes, each promoting a limited range of chemical reactions. A fundamental difference between enzymes and industrial catalysts is that enzymes function at physiological temperatures in a low ionic strength solution at near neutral pH. Nevertheless, enzymes are efficient catalysts. One molecule of the enzyme catalase can, for example, decompose approximately 40,000 molecules of hydrogen peroxide per second at about 0° C.

An important feature of enzymes is that they possess specific 3-D configurations that are fundamental to their biological function. This is because the overall shape of the molecule stabilizes the precise geometric structure of the "active site" (i.e., the region in the enzyme where the substrate is converted into the product). Without being tied to one theory, it is believed that in some cases the active site accelerates a reaction rate by stabilizing the transition state between the substrate and its products, thus lowering the activation energy for the reaction. For example, lowering the activation energy by about 34 kJ mol$^{-1}$ can increase the rate of a reaction by about a million fold at 298 K.

The activation energy for the enzyme catalyzed reaction can be determined by the Arrhenius equation:

$$k=Z_e^{-E_a/RT} \quad \text{Formula 1}$$

where k is the rate constant, $Z_e$ is a factor accounting for the frequency of collisions, R is the Gas constant, T is the absolute temperature in degrees Kelvin, and $E_a$ is the activation energy of the reaction. The activation energy for a given reaction may be determined by measurement of the reaction rate at different temperatures (limited to the thermal stability range of the enzyme) and plotting ln·k against 1/T.

Each enzyme typically requires certain conditions for optimum performance, particularly as regards to pH, temperature, and ionic strength. The presence of certain accessory substances (co-factors, activators, etc.) may also be useful, although not required, for optimal enzyme function.

The active site of many enzymes includes redox active groups that, for example, may be protonated or deprotonated depending on the redox state of the enzyme. Other well-known redox active sites include active site sulfides, metals such as iron, manganese, cobalt, and the like, iron-sulfur clusters, and hemes (e.g., iron hemes and cobalt hemes). Normally the redox state of an enzyme is a function of the pH, temperature, the ionic state, and/or chemical and physical factors affecting the redox state of the enzyme. As mentioned above, however, an electrical potential can be used to activate the redox groups in an enzyme active site and, thus, enhance the activity of an enzyme.

Enzymes that have shown activity towards BPA include, but are not limited to, ligninases such as laccase, manganese peroxidase (MnP), lignin peroxidase, versatile peroxidase, and the like. Ligninases such as laccase, manganese peroxidase (MnP), lignin peroxidase, and the like often found in certain fungi bacteria and are used to degrade the wood polysaccharide lignin.

Lignin is chemically recalcitrant to breakdown by most organisms because of its complex, heterogeneous structure. However, certain species of fungi (e.g., white rot fungi) produce an array of extracellular oxidative enzymes that synergistically and efficiently degrade lignin. The major groups of ligninolytic enzymes include lignin peroxidases, manganese peroxidases, versatile peroxidases, and laccases. The peroxidases are heme-containing enzymes with catalytic cycles that involve the activation by $H_2O_2$ and substrate reduction of compound intermediates. Lignin peroxidases have the unique ability to catalyze oxidative cleavage of C—C bonds and ether (C—O—C) bonds in non-phenolic aromatic substrates of high redox potential. Manganese peroxidases oxidize Mn(II) to Mn(III), which facilitates the degradation of phenolic compounds or, in turn, oxidizes a second mediator for the breakdown of non-phenolic compounds. Versatile peroxidases are hybrids of lignin peroxidase and manganese peroxidase with a bifunctional characteristic. Laccases are multi-copper-containing proteins that catalyze the oxidation of phenolic substrates with concomitant reduction of molecular oxygen to water. Among these, only laccase can catalyze $O_2$ dependent oxidation, whereas the other two types need $H_2O_2$ for their oxidative catalysis. These enzymes are being increasingly evaluated for a variety of biotechnological applications due to their broad substrate range. Additional discussion of ligninases, laccases and the like can be found in "Structure and Action Mechanism of Ligninolytic Enzymes." Domenic W. S. Wong, Appl. Biochem. Biotechnol. (2009), vol. 157, pp. 174-209, and "Laccases: a never ending story," Giardina et al., Cell. Mol. Life. Sci., (2010), vol. 67. pp. 369-385, the entireties of which are incorporated herein by reference.

A number of groups have reported the activity of MnP, laccases, and ligninases toward BPA. In one report, MnP and laccase were applied to remove the estrogenic activity of BPA and nonylphenol (NP). Both chemicals disappeared in the reaction mixture within a 1-h treatment with MnP but the estrogenic activities of BPA and NP still remained 40% and 60% in the reaction mixtures after a 1-h and a 3-h treatment, respectively. Extension of the treatment time to 12 h completed the removal of estrogenic activities of BPA and NP. Laccase has less ability to remove these activities than MnP, but a laccase-HBT (1-hydroxybenzotriazole) system was able to remove the activities in 6 h. A gel permeation chromatography (GPC) analysis revealed that main reaction products of BPA and NP may be oligomers formed by the action of enzymes. Enzymatic treatments extended to 48 h did not regenerate the estrogenic activities, suggesting that the ligninolytic enzymes are effective for the removal of the estrogenic activities of BPA and NP. Further discussion of the BPA degrading activity of manganese peroxidase (MnP) and laccases see, for example, "Degradation Pathway of Bisphenol A: Does ipso Substitution Apply to Phenols Containing a Quaternary a-Carbon Structure in the para Position?," B. Kolvenbach et al., Appl Environ Microbiol. 2007 August; 73(15): 4776-4784 and "Removal of Estrogenic Activities of Bisphenol A and Nonylphenol By Oxidative Enzymes From Lignin-Degrading Basidiomycetes," Tsutsumi et al., Chromosphere (2001), vol. 42, pp 271-276, the entireties of which are incorporated herein by reference.

Typically, the progress of the enzyme reaction (which is related to the concentration of analyte) is monitored by the rate of formation of product or the disappearance of a reactant. If either the product or reactant are electroactive, then the progress of the reaction can be monitored directly using amperometry. In the amperometry technique, current flow is measured in response to an applied voltage.

The use of mediators (e.g., molecules that can shuttle electrons between a redox centre of an enzyme and an electrode) can facilitate the function of an enzyme electrode. For example, the use of mediators can allow an enzyme on an enzyme electrode to be regenerated at an electrical potential where interference from species such as but not limited to ascorbate, urate, and paracetamol may normally interfere. A vast number of compounds are capable of acting as enzyme mediators.

Mediators may include coenzymes and/or compounds that can shuttle electrons and/or reactant or products from the electrode to the enzyme. Suitable examples of enzyme mediators for enhancing enzyme activity may include 1-hydroxybenzotriazole (HBT), a quinone, a ferrocene compound, tetrathiofulvalene (TTF), a osmium complex, an organic dye, a phthalocyanine, ferrocyanide, a polypyrrole, 7,7,8,8-tetracyanoquinodimethane (TCNQ), NADH, NADPH, FAD, FADPH, derivatives thereof, and combinations thereof. Arguably the most important examples of this class are mediators based on ferrocene and its derivatives, and this can be attributed to three main factors—they have a wide range of redox potentials, the redox potentials are independent of pH, and the synthetic schemes involved in making derivatives are usually straightforward.

II. Preparation of an Enzyme Electrode

In one embodiment, an enzyme electrode system configured for detecting and/or degrading bisphenol-A (BPA) is disclosed. The enzyme electrode system may include a working electrode and an enzyme capable of reacting with BPA linked to the working electrode. As discussed in greater detail above, suitable examples of enzymes that can be immobilized to the working electrode include, but are not limited to, ligninases such as laccase, manganese peroxidase (MnP), lignin peroxidase, and the like.

In one embodiment, the electrode system may include an electrically insulating base plate, a working electrode, and a counter electrode. In one aspect, the counter electrode may serve as a reference electrode configured to provide a reference voltage. In one embodiment, the electrode system may further include a separate reference electrode in addition to the working electrode and the counter electrode.

The proper functioning of an enzyme electrode is at least partially dependent on both the chemical and physical properties of the enzyme linked to the working electrode. To this end, there are many possible methods for immobilizing an enzyme at the surface of an electrode. Although there are many methods available for attaching an enzyme to an electrode, the method of choice will depend on the component and on the substrate to which it is to be attached.

In one example, the working electrode includes a carbon electrode, a porous silica gel film linked to the carbon electrode, and a gel material (e.g., an electropolymerized film) configured for linking the enzyme to the electrode and for promoting transfer of electrons to the enzyme.

For example, enzyme can be linked to an electrode by applying a gel material to the surface of an electrode and absorbing enzyme into the gel layer. Suitable examples of gel materials include one or more of, gelatin, cross-linked gelatin, poly(1,3-phenyl diamine), polythiophene, polyphenol, polyaniline, polyvinylpyrrolidone (PVP), monoolein, and poly(1,2-phenyl diamine).

In a specific example, laccase enzyme was immobilized onto an electrode system by electropolymerizing aniline onto the surface of an electrode to form a polyaniline layer. Laccase was subsequently absorbed into the polyaniline layer to form an enzyme electrode. Further discussion of this procedure can be found in "Thick Film Sensors Based on Laccases From Different Sources Immobilized in Polyaniline Matrix," Timur et al., Sensors and Actuators B (2004) vol. 97, pp. 132-136, the entirety of which is incorporated herein by reference.

In another specific example, laccase enzyme was crosslinked with glutaraldehyde, lyophilize, mixed with PVP, applied to a cellophane membrane, and partially dried. The enzyme, PVP, and the cellophane membrane were then applied to an electrode to form an enzyme electrode. Further discussion of this procedure can be found in "Biosensor for the Determination of Phenols Based on Cross-linked Enzyme Crystals (CLEC) of Laccase," Jegan Roy et al., Biosensors and Bioelectronics (2005) vol. 21, pp. 206-211, the entirety of which is incorporated herein by reference.

In yet another specific example, a laccase enzyme solution was added to melted monoolein and used to prepare a liquid crystal phase of the enzyme. The monoolein-based enzyme liquid crystal could then be applied to an electrode. Further discussion of this procedure can be found in "Properties of Native and Hydrophobic Laccases Immobilized in the Liquid-Crystalline Cubic Phase on Electrodes," Nazaruk et al., J. Biol. Inorg. Chem. (2007) vol. 12, 335-344, the entirety of which is incorporated herein by reference.

In one embodiment, the enzyme electrode system may further include an entrapment layer configured to at least partially maintain linkage between the enzyme and the working electrode. The entrapment layer is not especially limited as long as the layer, for example, prevents the outflows of the enzyme immobilized in the electrode system and permits transport of reactants and products. To put it concretely, the entrapment layer may be, for example, hydrophilic or hydrophobic, may be an inorganic substance or an organic substance, may be a porous material or a fibrous material, may be a polymeric gel, may be a photo-crosslinking resin, or another immobilization material known by persons having skill in the art.

In one aspect, an example of an entrapment layer may include a semi-permeable membrane such as a dialysis membrane. A dialysis membrane having a suitable molecular weight cut-off is well suited for serving as an entrapment layer in that it is capable of permitting small molecules (e.g., reactants and products) to diffuse into and out of the electrode system while preventing the enzyme from diffusing away from the electrode. A suitable molecular weight cut-off may be about 1000 molecular mass units (mmu), about 2000 mmu, about 3000 mmu, about 4000 mmu, about 5000 mmu, about 10,000 mmu, or about 15,000 mmu, or any suitable amount less than the mass of the enzyme immobilized on the electrode. For instance, a quantity of enzymes in a suitable volume of buffer can be applied to the surface of an electrode. The electrode can then be covered with a 20-25 mm thick dialysis membrane, of about 10,000 Daltons molecular weight cut-off and held in place by a suitably sized o-ring. For a specific example of the use of a dialysis membrane as an entrapment layer, see "Biosensor for the Determination of Phenols Based on Cross-linked Enzyme Crystals (CLEC) of Laccase," Jegan Roy et al., Biosensors and Bioelectronics (2005) vol. 21, pp. 206-211, which was incorporated above by specific reference.

In another example, an entrapment layer may include reactive groups that are capable of forming one or more covalent bonds with the immobilized enzymes. For example, the entrapment layer may include reactive carboxyl groups that can form amide bonds with the enzymes by reacting with the amine groups included in the enzymes. Diffusion of the enzyme out of the electrode system may thereby be prevented.

To put it concretely, for example, a predetermined cross-linking agent may be introduced into the entrapment layer such that the enzymes may be immobilized by the cross-linkage of the conductive polymeric molecules. Alternatively, the enzymes may be immobilized by the cross-linkage of glutaraldehyde or the like, or the enzymes may be immobilized by the cross-linkage of a photo-crosslinking resin or the like.

For example, when the conductive polymeric molecules, such as polyaniline molecules, are cross-linked together with the enzymes, then the conductive polymeric molecules becomes a network structure through a plurality of cross-linked parts. Thereby, the electrode structure can be physically strengthened, and, at the same time, the surface area of the electrode can be increased. Consequently, the sensitivity of the enzyme electrode and the response time can be improved. In a specific example, laccase enzyme was mixed with gelatin and allowed to partially dry. The partially dried enzyme/gelatin matrix was then cross-linked with glutaraldehyde solution and the cross-linked matrix was applied to an electrode. This system cross-links the gelatin and the enzyme together to form a cross-linked matrix that is capable of immobilizing the enzyme onto the electrode. For further discussion of this procedure, see "Laccase Biosensors Based on Mercury Thin-Film Electrode," Kurgõz et al., Artificial Cells, Blood Substitutes, and Biotechnology (2005) vol. 33, 447-456.

In one embodiment, the working electrode may include a mesh layer configured for increasing the surface area of the working electrode. Suitable examples of mesh layers include nylon mesh material, platinum mesh, or metal plated cloth material (e.g., gold or platinum plated nylon or polyester mesh). In one embodiment, the thread count (i.e., the number of threads or strands per unit area) of the mesh material may be about 50 to about 1000 threads per centimeter (TPC), about 100 to about 900 TPC, about 150 to about 800 TPC, about 200 to about 700 TPC, about 250 to about 600 TPC, about 300 to about 500 TPC, or any number therebetween. A specific example of a mesh electrode that can be used in electrochemical applications can be found in U.S. Pat. No. 6,267,866, the entirety of which is incorporated herein by reference. The enzyme can be immobilized to a mesh electrode using any of the methods described briefly herein and further described in the references incorporated by reference above.

In one embodiment, the enzyme electrode system may further include a working electrode that includes a carbon nanotube layer configured for increasing the surface area and the response of the electrode. For example, the carbon nanotube layer may include a plurality of carbon nanotubes coupled to the working electrode and immobilized thereon, the enzyme capable of degrading BPA immobilized in the carbon nanotube layer by being sandwiched between the carbon nanotubes. Specific examples of electrode systems that include carbon nanotubes can be found in "Carbon Nanotube-Based Biosensor," Wohlstadter et al., Advanced Materials (2003), vol. 15, no. 14, pp. 1184-1187; "A Novel Amperometric Sensor and Chromatographic Detector for Determination of Parathion," Li et al., (2005) vol. 381, pp. 1049-1055; and "Mercury-Free Simultaneous Determination of Cadmium and Lead at a Glassy Carbon Electrode Modified With Multi-Wall Carbon Nanotubes," Wu et al., Analytica Chemica Acta (2003) vol. 489, pp. 215-221, the entireties of which are incorporated herein by reference.

Carbon nanotubes (CNTs) are allotropes of carbon with a cylindrical nanostructure. Nanotubes are categorized as single-walled nanotubes (SWNTs) and multi-walled nanotubes (MWNTs). The diameter of a nanotube is on the order of a few nanometers, while they can be up to several millimeters in length. Nanotubes have been constructed with length-to-diameter ratio of up to 28,000,000:1, which is significantly larger than any other material. Because of their extraordinary length-to-diameter ratio, carbon nanotubes can have an extraordinarily high surface area.

Carbon nanotubes have novel properties that make them potentially useful in many electrical applications. For example, because of the symmetry and unique electronic structure of graphene, the structure of a carbon nanotube strongly affects its electrical properties. For example, a given nanotube may be metallic or semiconducting. In theory, metallic nanotubes can carry an electrical current density of $4 \times 10^9$ A/cm$^2$, which is more than 1,000 times greater than metals such as copper. Because of their extraordinary surface area and electrical properties, carbon nanotubes can be used to increase the activity and response of an enzyme electrode.

FIG. 1A depicts a schematic of an embodiment of an enzyme electrode and FIG. 1B depicts a cut-away view of the enzyme electrode of FIG. 1A taken along line 1B-1B. As shown in FIGS. 1A and 1B, an example of an enzyme electrode 100 includes, for example, a substrate 102, an analysis section 104 provided on the top surface of the substrate 102. The analysis section 104 includes an opening portion on the top surface thereof, a hydrophobic insulation film 106 provided around the analysis section 104 on the top surface of the substrate 102, a working electrode 120, a counter electrode 108, a reference electrode 110, these three electrodes being positioned in the analysis section 104 on the top surface of the substrate 102, and electrical connecting pads 116a-116c connected to the working electrode 120, the counter electrode 108, and the reference electrode 110, respectively, with wiring 118, as shown in FIGS. 1A and 1B.

As discussed elsewhere herein, the working electrode can include an enzyme capable of reacting with BPA that is linked to the working electrode. Suitable examples of enzymes that can be linked to the working electrode include, but are not limited to, manganese peroxidase (MnP), laccase, and ligninase, and the like.

In one example, the working electrode includes a carbon electrode 122, a porous silica gel film 124 linked to the carbon electrode 122, an electropolymerized film 126 linked to the porous silica gel film 124, and an enzyme layer 128 linked to the working electrode 120. In one aspect, the electropolymerized film 126 can be configured for linking the enzyme layer 128 to the working electrode and promoting transfer of electrons to the enzyme layer 128 linked to the working electrode. Suitable examples of electropolymerized films include one or more of poly(1,3-phenyl diamine), polythiophene, polyphenol, polyaniline, and poly(1,2-phenyl diamine).

The carbon electrode 122 is linked to electrical lead 118a, which is in turn linked to electrical connecting pad 116a. As shown in FIG. 1B, an insulator 114 surrounds the carbon electrode 122, the porous silica gel film 124, the electropolymerized film 126, and the enzyme layer 128.

In one embodiment, the working electrode 120 may further include an entrapment layer 112 configured to at least partially maintain linkage between the enzyme and the working electrode. The entrapment layer 112 is not especially limited as long as the layer, for example, prevents the outflows of the enzyme immobilized in the working electrode and permits transport of reactants and products. The entrapment layer 112 may be, for example, hydrophilic or hydrophobic, may be an inorganic substance or an organic substance, may be a porous material or a fibrous material, may be a polymeric gel, may be a photo-crosslinking resin, or another immobilization material known by persons having skill in the art.

In one embodiment, the working electrode 120 may further include a mesh layer configured for increasing the surface area of the working electrode. According to one embodiment, one or more components of the working electrode 120 can be positioned on or incorporated into the mesh layer. For example, the mesh layer may be placed in addition to or in lieu of the carbon electrode 122. Suitable examples of mesh layers include nylon mesh material, platinum mesh, or metal plated cloth material (e.g., gold or platinum plated nylon or polyester mesh).

In another embodiment, the working electrode may further include a carbon nanotube layer configured for increasing the surface area and the response of the electrode. In one aspect, the carbon nanotube layer may include a plurality of carbon nanotubes coupled to the working electrode and immobilized thereon, the enzyme capable of degrading BPA immobilized in the carbon nanotube layer by being sandwiched between the carbon nanotubes. According to one embodiment, carbon nanotubes can be incorporated into or placed in lieu of one or more of the components of the working electrode 120. For example, the carbon nanotube layer may be placed in addition to or in lieu of one or more of the carbon electrode 122, the porous silica gel film 124, or the electropolymerized film 126.

FIG. 2 illustrates a schematic of an embodiment of an enzyme electrode that enables degradation of bisphenol-A (BPA) and/or monitoring of BPA concentration in contaminated water. Apparatus 200 of FIG. 2 can be used to monitor for the presence of BPA in contaminated water and/or to degrade BPA in contaminated water. For example, monitoring for the presence of BPA in water that may be contaminated can be used as an indication of whether or not the water is safe to drink. Degrading BPA in contaminated water can remove the estrogenic and other endocrine activity caused by BPA contamination and render the water safe for drinking.

In one embodiment, the apparatus 200 includes a fluid reservoir 202 and an electrode system 204 that includes an enzyme electrode 100 and a power source 206 that is capable of providing a voltage to the enzyme electrode 100 and of monitoring the current flow through the apparatus 200. The fluid reservoir 202 can be essentially any container capable of containing a fluid. Preferably the fluid reservoir 202 is a non-conductive container (e.g., plastic or glass) that does not itself contain BPA. Suitable examples include bottles, pitchers, home water tanks, building water tanks, municipal water tanks, and the like. While FIG. 2 illustrates apparatus 200 includes a water reservoir 202, one will appreciate that the enzyme electrode 100 could be placed "in-line," such as, but not limited to, in a home water faucet.

In one embodiment, the enzyme electrode 100 includes a working electrode 120, a counter electrode 108, and a reference electrode 110. The power source includes a potentiostat 208 for applying a set forward voltage to the enzyme electrode 100 and a current meter 210 to monitor current flow through the apparatus 200. The enzyme electrode 100 is connected to the power supply 206 by virtue of electrical lead 216 that is connected to the one of the electrical connecting pads 116a-116c of the working electrode 120.

In order to measure degradation of BPA, a two-electrode system including only a working electrode and a counter electrode and a three-electrode system further including a reference electrode in addition to the two electrodes may be used. The latter facilitates more precise measurements.

In one example, the degradation of BPA can be monitored coulometrically. Coulometry is the name given to a group of techniques in analytical chemistry that determine the amount of matter transformed during an electrolysis reaction by measuring the amount of electricity (in coulombs) consumed or produced in the redox reaction.

There are two basic categories of coulometric techniques. Potentiostatic coulometry involves holding the electric potential constant during the reaction using a potentiostat. The other, called coulometric titration or amperostatic coulometry, keeps the current (measured in amperes) constant using an amperostat.

Potentiostatic coulometry is a technique most commonly referred to as "bulk electrolysis." The working electrode is kept at a constant potential and the current that flows through the circuit (e.g., apparatus 200) is measured. This constant potential is applied long enough to fully reduce or oxidize all of the substrate in a given solution. As the substrate is consumed, the current also decreases, approaching zero when the conversion is complete. The sample mass, molecular mass, number of electrons in the electrode reaction, and number of electrons passed during the experiment are all related by Faraday's laws. It follows that, if three of the values are known, then the fourth can be calculated. Bulk electrolysis is often used to unambiguously assign the number of electrons consumed in a reaction observed through voltammetry. It is estimated that BPA detection limits for the system are in the $\mu A$ to nA at the ppm level and nA to pA at the ppb level.

The rate of such reactions is not determined by the concentration of the solution, but rather the mass transfer of the substrate in the solution to the electrode surface. Rates will increase when the volume of the solution is decreased, the solution is stirred more rapidly, or the area of the working electrode is increased.

Coulometric titrations use a constant current system to accurately quantify the concentration of a species, with the applied current being equivalent to a titrant. Current is applied to the unknown solution until all of the unknown species is either oxidized or reduced to a new state, at which point the potential of the working electrode shifts dramatically. This potential shift indicates the endpoint. The magnitude of the current (in amps) and the duration of the current (seconds) can be used to determine the moles of the unknown species (e.g., BPA) in solution. When the volume of the solution is known, then the molarity of the unknown species can be determined.

In another example, amperometry can be used to monitor for the presence and/or the concentration of BPA in water. Amperometric titration refers to a class of titrations in which the equivalence point is determined through measurement of the electric current produced by the titration reaction.

Consider a solution containing BPA. If an electrolytic potential is applied to the solution through a working electrode, then the measured current depends (in part) on the concentration of the BPA. Because of the specificity of the enzyme electrode for BPA, the current flow through the system will be highly dependent on the presence of BPA. Measurement of this current can be used to determine the presence of or the concentration of the BPA directly. That is, the electrode is configured to adjust the redox state of the enzyme and enhance the activity of the enzyme. The enzyme breaks BPA down by the natural chemical function of the enzyme because BPA is a substrate for the enzyme. BPA degradation produces conductive species that can be detected by the electrode.

One will appreciate that the electrode system can also be used to degrade BPA in water that is known to be contaminated. For example, a voltage of about −1 V to about 1 V, or −0.75 V to about 0.75 V, or about −0.5 V to about 0.5 V, or about −0.25 V to about 0.5 V, or about 0.25 to about 0.5 V can be applied to the system in order to activate the enzyme and accelerate degradation of the BPA in the contaminated sample. The time necessary for decontaminating water depends on the concentration of BPA in the initial sample. For example, a sample of water could be decontaminated in a period of time ranging from about 10 minutes to about 500 minutes, or about 20 minutes to about 400 minutes, about 30 minutes to about 300 minutes, or about 40 minutes to about 250 minutes, or about 60 minutes to about 120 minutes. Specific examples of the use of electrochemical methods for monitoring substances can be found in "Development of Coulometry and Its Application to Food Analysis," Shun-ichi UCHIYAMA, Chemical Sensors (1995) vol. 11, no. 1 and "Electrocatalytic Degradation of Chlorinated Phenolic Compound with Laccase-Modified Polyaniline/Silica Sol-Gel/Carbon Composite Electrodes," Res. Bull. Fukuoka Inst. Tech., Ota et al., (2007) vol. 40, no. 1, pp 21-27, the entireties of which are incorporated by reference.

III. Methods Detecting and/or Degrading Bisphenol-A

In one embodiment, a method for detecting and/or degrading bisphenol-A (BPA) is disclosed. The method may include providing an electrode system that includes an enzyme capable of reacting with BPA immobilized to the electrode system, immersing the electrode system in a sample, and applying a voltage to the electrode system to promote detection and/or degradation of BPA. In one embodiment, the enzyme immobilized to the electrode system includes at least one of manganese peroxidase (MnP), laccase, or ligninase.

In one embodiment, the electrode system may include an electrically insulating base plate, a working electrode, and a counter electrode, and wherein the working electrode includes a carbon electrode, a porous silica gel film linked to the carbon electrode, and an electropolymerized film configured for promoting transfer of electrons to the enzyme immobilized to the working electrode.

In one embodiment, the working electrode may further include one or more of an electrically conductive mesh layer, a carbon nanotube layer including a plurality of carbon nanotubes immobilized to the working electrode.

In one embodiment, the sample can be and aqueous medium that is suspected of being contaminated with BPA. Suitable examples of samples include, but are not limited to, drinking water, fruit juices, canned foods (e.g., canned tomatoes), sauces, and the like. In another embodiment, the sample can include a control sample in addition to or in lieu of a sample suspected of being contaminated with BPA. Suitable examples of control samples include, but are not limited to, samples known to contain no appreciable BPA and/or samples containing a known amount of BPA.

In one embodiment, the method can further include immersing the electrode system in an aqueous solution for a period of time sufficient to degrade the BPA below a selected concentration level. One will appreciate that the time necessary sufficient for degrading the BPA below a selected concentration level water may depend either on the on the concentration of BPA in the initial sample, the selected concentration level for BPA following treatment, or both. For example, a sample of water could be decontaminated in a period of time ranging from about 10 minutes to about 500 minutes, or about 20 minutes to about 400 minutes, about 30 minutes to about 300 minutes, or about 40 minutes to about 250 minutes, or about 60 minutes to about 120 minutes.

The selected level of concentration for BPA in decontaminated water is somewhat controversial. The United States Environmental Protection Agency (USEPA) currently considers a "safe" level of exposure to BPA to be about 50 micrograms per kilogram of body weight per day. If a person were only exposed to BPA through contaminated tap water, the USEPA's safe level would translate to a concentration level of about 1 to 2 ppm for a person who consumes about 1 to 2 liters of water per day. Nevertheless, BPA has been shown to have estrogen-like activity at concentrations as low as the part-per-trillion range, which is lower than concentrations commonly found in the blood of human infants, children, and adults. As such, the selected level of concentration for BPA in decontaminated water may be in the range of about 1-2 parts-per-million, parts-per-billion, parts-per-trillion, or even lower.

The time needed to lower the concentration of BPA in a contaminated sample is dependent on number of factors including, but not limited to, volume of the sample, amount (activity) of enzyme, surface area of electrode(s), amount of BPA in the sample, and the like. "Electrocatalytic Degradation of Chlorinated Phenolic Compound with Laccase-Modified Polyaniline/Silica Sol-Gel/Carbon Composite Electrodes," Res. Bull. Fukuoka Inst. Tech., Ota et al., (2007) vol. 40, no. 1, pp 21-27, which was incorporated by reference above discusses the degradation of 4C2M (4-chloro-2-methoxyphenol) with an enzyme electrode. Based on the results of Ota et al., assuming that the substrate is BPA instead of 4C2M, BPA in aqueous solution should be decreased by 20-30% in approximately 250 minutes of reaction time under the following conditions:

Conc. of BPA: 0.1 mM (approx. 23 mg/L or 23 ppm)
Volume of aqueous solution: 15 mL
Amount of coated laccase on the electrode: 80 U/mg
Electrical potential applied: +0.5 V In one embodiment, the method may further include applying a voltage to activate the enzyme and accelerate degradation of the BPA in the contaminated sample. In practice, the range of applied voltages that can be used to activate the enzyme are a function of the enzyme used, the mediators and co-factors present in the solution, pH, and the ionic strength of the solution. The range of voltages that can be used to activate the enzyme can be determined empirically using a technique such as cyclic voltammetry to determine the potential or potentials at which activity of the enzyme or enzymes peak(s). For example, manganese peroxidase will not necessarily be activated or be stable at a voltage used to activate laccase. Typical voltages that can be used with the enzymes discussed herein to activate the enzyme and accelerate degradation of the BPA in the contaminated sample include, but are not limited to, about −1 V to about 1 V, or −0.75 V to about 0.75 V, or about −0.5 V to about 0.5 V, or about −0.25 V to about 0.5 V, or about 0.25 V to about 0.5 V. Further discussion of the electrochemical properties of ligninases such as laccase, manganese peroxidase (MnP), lignin peroxidase, versatile peroxidase, and the like can be found in Wong et al., Giardina et al., and Tsutsumi et al., which were incorporated by reference above.

In another embodiment, a method for degrading bisphenol-A (BPA) is disclosed. The method may include providing an electrode system that includes an electrically insulating base plate, a working electrode, a counter electrode, and an enzyme selected from the group consisting of manganese peroxidase (MnP), laccase, ligninase, and combinations thereof immobilized to the working electrode, wherein the working electrode includes a carbon electrode, a porous silica gel film linked to the carbon electrode, and an electropolymerized film configured for promoting transfer of electrons to the enzyme immobilized to the working electrode. The method further includes immersing the electrode system in an aqueous medium suspected of being contaminated with BPA applying a voltage in a range from about −1 V to about 1 V to the electrode system for a period of time sufficient to degrade the BPA below a selected concentration level.

The present disclosure is not to be limited in terms of the particular examples described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular examples only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, the term "substantially" is used to mean to a great extent or degree. The term "substantially" is often used in conjunction with another term to describe the extent or degree of that term such as, but not limited to, angles, shapes, and states of being. For example, the term "substantially perpendicular" may be used to indicate some degree of leeway in an angular measurement. That is, an angle that is "substantially perpendicular" may be 90°, but angles such as 45°, 60°, 65°, 70°, 75°, 80°, 85°, 95°, 100°, 105°, 110°, 115°, 120°, 125°, 130°, or 135° may also be considered to be "substantially perpendicular." Similarly, "substantially" may be used in conjunction with a shape term such as "substantially cylindrical" to indicate that the object referred to may have a circular profile or an ovoid profile. Likewise, a term describing a state of being such as the term "substantially closed," may be used to indicate that something is mostly closed or usually closed, but that it need not be 100% closed or always closed.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An enzyme electrode system configured for detecting and/or degrading bisphenol-A (BPA), comprising:
   a building water reservoir configured to receive and dispense drinking water;
   the enzyme electrode comprising:
      a working electrode;
      a porous silica Gel film linked to the working electrode;
      a electropolymerized film material linked to the porous silica gel film;
      an enzyme configured to react with BPA linked to the working electrode by being located in the electropolymerized film material, wherein the enzyme includes one or more of manganese peroxidase (MnP), lignin peroxidase, or versatile peroxidase; and
      a coenzyme and/or enzyme mediator contained in the electropolymerized film material and operatively coupled to the working electrode and the enzyme, wherein the coenzyme and/or enzyme mediator is selected from the group consisting of 1-hydroxybenzotriazole (HBT), a ferrocene compound, tetrathiofulvalene (TTF), an osmium complex, an organic dye, a phthalocyanine, ferrocyanide, a polypyrrole, 7,7,8,8-tetracyanoquinodimethane (TCNQ), NADH, NADPH, FAD, FADPH, and combinations thereof;

wherein the enzyme electrode system is configured to operate at a voltage of about +0.25V to about +1 V for detecting and/or degrading BPA; and wherein the enzyme electrode is positioned in the building water reservoir so as to detect and/or degrade the BPA in the drinking water in the building water reservoir.

2. The enzyme electrode system of claim 1, comprising:

an electrically insulating base plate;

the working electrode located on the insulating base plate; and a counter electrode located on the insulating base plate separated from the working electrode.

3. The enzyme electrode system of claim 2, further comprising a reference electrode located on the insulating base plate separated from the working electrode and/or the counter electrode.

4. The enzyme electrode system of claim 1, wherein the electrode of the working electrode includes a carbon electrode.

5. The enzyme electrode system of claim 1, wherein the electropolymerized film includes one or more of poly(1,3-phenyl diamine), polythiophene, polyphenol, polyaniline, or poly(1,2-phenyl diamine).

6. The enzyme electrode system of claim 1, wherein the working electrode includes an electrically conductive mesh layer configured for increasing the surface area of the working electrode.

7. The enzyme electrode system of claim 1, further comprising an entrapment layer configured to at least partially maintain linkage between the enzyme and the working electrode.

8. The enzyme electrode system of claim 1, wherein the building water reservoir includes a water faucet, the enzyme electrode being in fluid contact with water flowing through the water faucet so as to detect and/or degrade BPA in the water flowing therethrough.

9. The enzyme electrode system of claim 8, wherein the enzyme electrode is disposed in a water flow path of the water faucet so as to detect and/or degrade BPA in water flowing through the faucet.

* * * * *

UNITED STATES PATENT AND TRADEMARK OFFICE
CERTIFICATE OF CORRECTION

PATENT NO. : 9,206,459 B2
APPLICATION NO. : 12/999469
DATED : December 8, 2015
INVENTOR(S) : Oguchi Page 1 of 1

It is certified that error appears in the above-identified patent and that said Letters Patent is hereby corrected as shown below:

In The Specification

In Column 1, Line 8, delete "371" and insert -- § 371 --, therefor.

In Column 4, Line 21, delete "Life." and insert -- Life --, therefor.

In The Claims

In Column 14, Line 50, in Claim 1, delete "Gel" and insert -- gel --, therefor.

In Column 14, Line 51, in Claim 1, delete "a" and insert -- an --, therefor.

In Column 14, Line 62, in Claim 1, delete "of1" and insert -- of 1 --, therefor.

Signed and Sealed this
Tenth Day of May, 2016

Michelle K. Lee
*Director of the United States Patent and Trademark Office*